United States Patent [19]

Tamura et al.

[11] 4,052,442

[45] Oct. 4, 1977

[54] PROCESS FOR PREPARING GLYCOL ESTERS

[75] Inventors: Masuhiko Tamura; Teruo Yasui, both of Kurashiki, Japan

[73] Assignee: Kuraray Co. Ltd., Japan

[21] Appl. No.: 608,756

[22] Filed: Jan. 12, 1967

[30] Foreign Application Priority Data

Jan. 21, 1966  Japan .................................. 41-3557
Aug. 25, 1966  Japan .................................. 41-56170

[51] Int. Cl.$^2$ ............................................. C07C 67/05
[52] U.S. Cl. ..................................... 560/243; 560/112
[58] Field of Search ............. 260/497 A, 476, 410.9 U

[56] References Cited

U.S. PATENT DOCUMENTS

| | | | |
|---|---|---|---|
| 3,346,624 | 10/1967 | Schaeffer | 260/497 |
| 3,349,118 | 10/1967 | Kohll et al. | 260/497 |
| 3,859,336 | 1/1975 | Aguilo | 260/497 A |

*Primary Examiner*—Lorraine A. Weinberger
*Assistant Examiner*—Michael Shippen
*Attorney, Agent, or Firm*—Sherman & Shalloway

[57] ABSTRACT

A process for preparing glycol esters such as ethylene glycol diacetate which comprises contacting a monoolefin such as ethylene with an organic monocarboxylic acid such as acetic acid containing a palladous salt and either a nitrate or a nitrite.

15 Claims, No Drawings

PROCESS FOR PREPARING GLYCOL ESTERS

This invention relates to a process for preparing glycol esters by oxidizing monoolefins.

Recently, a process for preparing glycol esters has been reported which comprises contacting an ethylenically unsaturated compound with a compound of a noble metal of group VIII of the periodic table, in an anhydrous liquid medium, in the presence, based on the noble metal compound, of at least 80 mol % of nitric acid as oxydant (French Pat. No. 1419966). However, the activity of the catalyst system in this process is not necessarily high, nor is the yield of glycol esters to the ethylenically unsaturated compound and the nitric acid, which have been reacted, sufficiently high.

The object of this invention is therefore to provide a process for preparing glycol esters in good yield by using a catalyst system which has greater activity than that of hereinbefore noted prior art.

The foregoing object of this invention is achieved basically by a process for preparing glycol esters which comprises carrying out the reaction by introducing a monoolefin into a carboxylic acid containing a palladous salt and either a nitrate or nitrite.

Nitric acid, which is used in the foregoing prior art process, is one of most common oxydants that is used in various oxidative reactions in organic chemistry. On the other hand, the nitrates or nitrites, e.g., the nitrates or nitrites of the alkali or alkaline earth metals, the use of which is a most important feature of this invention, are substances which are stable at elevated temperatures of even 400° – 500° C., as can be seen from their wide use in the inorganic and organic chemical industries as "Niter", a heat transfer agent.

It would not be conceivable from the standpoint of common sense that these nitrates and nitrites which were even stable at elevated temperature would be capable of demonstrating their oxidative action under similar conditions of use as in the case of nitric acid. It was therefore a surprising fact to find that these nitrates and nitrites had a much greater activity and longer life than nitric acid in the preparation of glycol esters by oxidation of monoolefins even at temperatures below 100° C.

In fact, whereas the yield of glycol esters to the reacted olefins in the aforesaid prior art process does not attain 75%, it is possible according to this invention to prepare glycol esters in a yield as high as above 80% or even above 90%, based on the reacted olefins, by a suitable choice of the reaction conditions. This is illustrated by the following experiment.

A 4-necked 100-cc flask was charged with 50 cc of acetic acid, 0.8 millimole of palladous acetate and either 10 millimoles of nitric acid, 10 millimoles of lithium nitrate or 5 millimoles of cupric nitrate, after which the reaction was carried out while introducing at 45° C. as much as a mixed gas of ethylene and oxygen as would be absorbed. The results obtained by this experiment were as shown in Table I, below.

Table I

| | Amount Formed of Ethylene Glycol Monoacetate | |
|---|---|---|
| | After One Hour | After Three Hours |
| $HNO_3$ | 14 millimoles | 27 millimoles |
| $LiNO_3$ | 26 | 75 |
| $Cu(NO_3)_2$ | 21 | 63 |

Further, in another experiment the reaction was carried out by introducing ethylene for 2 hours at 90° C. to a solution consisting of 0.94 millimole of palladous acetate and 10 millimoles of nitric acid in 50 cc of acetic acid. In this case, the product consisted of 4.9 millimoles of ethylene glycol diacetate, 1 millimole of ethylene glycol monoacetate, 0.9 millimole of acetaldehyde and 1.2 millimoles of ethylidene diacetate. On the other hand, when the reaction was carried for 2 hours under identical conditions except that 10 millimoles of lithium nitrate was used instead of nitric acid, the product consisted of 11.6 millimoles of ethylene glycol diacetate, 3 millimoles of ethylene glycol monoacetate, 0.4 millimole of acetaldehyde, 0.4 millimole of ethylidene acetate and 0.1 millimole of vinyl acetate.

Further, as hereinafter described, the proportion formed of the glycol monoester and glycol diester can be changed optionally according to this invention by varying the reaction temperature and reaction time. For instance, it is possible to form essentially only monoesters. This is another point in which this invention excels the aforementioned prior art process.

The palladous salts used in this invention include, e.g., palladous chloride, palladous nitrate, palladous bromide, sodium palladium tetrachloride, palladous sulfate or the palladous salt of the carboxylic acid used, such as palladous acetate, preferred use being made of palladous chloride, palladous nitrate and palladous acetate. Again, it is also effective to add metallic palladium to the reaction system and form a palladous salt in situ. The concentration of the palladous salt is preferably at least 0.001% by weight of the reaction mixture, a range of 0.1 to 10% being particularly to be preferred. A concentration of the palladous salt of less than 0.001% by weight reduced the reaction rate, whereas a concentration greater than necessary lowers the yield of glycol esters to the reacted olefins.

Desirable nitrates or nitrites are exemplified by the salts of the metals of group I of the periodic table, e.g., lithium nitrate, sodium nitrate, sodium nitrite, potassium nitrite and cupric nitrate, the salt of the metals of group II of the periodic table, e.g., calcium nitrate, zinc nitrate and barium nitrate, and the salts of the metal of group VIII of the periodic table, e.g., ferric nitrate, cobalt nitrate and nickel nitrate. Of these, particularly to be recommended are the salts of alkali and alkaline earth metals, and especially the nitrates thereof. These salts can either be used alone or in combinations of two or more thereof.

The concentration of the nitrate or nitrite in the reaction mixture is effective if it is at least 0.001 mole/liter, the upper limit being preferably 5 moles/liter, and optimally not more than 2 moles/liter.

The rate at which the nitrate or nitrite is used to the palladous salt is preferably that wherein $NO_3$ or $NO_2$:Pd (mole ratio) is at least 1:1, particularly preferably at least 5:1, and optimally a range from 10:1 to 100:1. .

The catalyst system of the invention process is basically composed of (a) of palladous salt and (b) a nitrate or nitrite, but by using as supplements nitric acid, nitrous acid, organic acid salts of alkali metals or organic acid salts of alkaline earth metals the reaction rate can be increased. The organic acid salts of alkali or alkaline earth metals to be used for this purpose are preferably the salts of the carboxylic acid that is to be used as the reaction medium. For instance, when the reaction is carried out in acetic acid, the use of an acetate, such as lithium acetate, is to be preferred. For Example, when lithium acetate is added, a reaction rate fourfold that of the instance when not added is demonstrated, but there is an optimum value for the amount to be added. It is normally desirable that the amount added is equal or less than the amount of nitrate or nitrite used. The use of the carboxylate in an amount greatly in excess of the amount of nitrate or nitrite used results in the promotion of side reactions and is hence not desirable. This however does not apply when both nitric acid and nitrous acid are used together. Typical combinations of the catalyst components, as used in the invention process hereinbefore described, include such, for example, a (1) palladous chloride-sodium nitrate (or sodium nitrite), (2) palladous chloride-sodium nitrate (or sodium nitrate)-sodium acetate, (3) palladous chloride-sodium nitrate (or sodium nitrite)-sodium acetate-nitric acid (or nitrous acid), and (4) palladous chloride, sodium nitrate (or sodium nitrite)-nitric acid (or nitrous acid).

The carboxylic acids that can be used in this invention are the monocarboxylic acids of not more than 7 carbon atoms, such as acetic acid, propionic acid, butyric acid and benzoic acid, preferred being the saturated fatty acids of which acetic acid is especially to be preferred. This monocarboxylic acid may contain several mole percent, more specifically 5 – 7 mole %, of water without affecting the reaction. Neither do the presence of the various solvents such, for example, as nitrobenzene, which are inert under the reaction conditions, impede the reaction.

As monoolefins which can be used in this invention, those of not more than 8 carbon atoms such as the alpha-monoolefins, typical of which are ethylene, propylene and 1-butene and even styrene, are suitable, but for obtaining glycol esters which are especially valuable commercially ethylene and propylene are particularly to be preferred. These monoolefins need not be pure, the admixture of such inert gases a nitrogen and the saturated hydrocarbons such as methane and ethane having no effect whatsoever on the reaction. The reaction according to this invention can be carried out in the presence of oxygen. The use of oxygen serves to cause the action of the nitrates or nitrites to be more effective. In this case, the proportion of the oxygen and monoolefin can be chosen optionally. When considered from the standpoint of the reaction rate, the amount used of the oxygen is preferably a range from 1 to 50 mole % of the total of the monoolefin and oxygen, the optimum being from 10 to 45 mol %.

The feeding to the reaction system of such nitrogen oxides as nitronic oxide (NO), nitrogen dioxide ($NO_2$), nitrogen pentoxide ($N_2O_5$) or nitrogen trioxide ($N_2O_3$) is also useful in promoting the catalytic activity. The amount used of the nitrogen oxide is preferably 0.1 – 50 mol % based on the monoolefin. The most preferred nitrogen oxides are nitronic oxide and nitrogen dioxide. When the reaction is carried out with an olefin-oxygen mixed gas, especially desirable results are obtained by the use of these nitrogen oxides.

In practicing the invention process, if at least one of either a nitrate, nitrite, nitric acid or nitrous acid is continuously added to the reaction system during the progress of the reaction, the catalytic activity can be prolonged for an exceedingly lengthy period of time.

The reaction of this invention can be carried out at a temperature ranging between 20° and 150° C., but for obtaining the glycol esters in good yield a low temperature of not more than 120° C. is to be preferred. The proportion in which glycol monoesters and glycol diesters are formed can be varied optionally by changing the reaction temperature. For preparing glycol monoesters selectively, a temperature lower than 80° C. should be chosen, a range between 20° C and 75° C., being particularly desirable. On the other hand, at a temperature ranging between 80° and 100° C. a mixture of glycol monoesters and glycol diesters is obtained, while glycol diesters are selectively obtained when 100° C. is exceeded.

A reaction pressure of 1 – 10 atm is preferably used, the optimal pressure being 1 – 7 atm. It is not desirable to raise the reaction pressure more than necessary, since side reactions become pronounced.

The glycol esters prepared by the invention process can be used as starting material of a wide variety of commercially valuable compounds. For example, ethylene glycol diacetate becomes a starting material of acetic anhydride, acetone, acetaldehyde and vinyl acetate, when decomposed. On the other hand, in the case of ethylene glycol monoacetate, in its as-obtained state or upon being hydrolyzed to ethylene glycol, it not only is usable as the starting material of polyesters but is also useful as an antifreeze.

The following nonlimitative examples are given for illustrating this invention.

EXAMPLE 1

After dissolving 50 cc of glacial acetic acid, 5.3 millimoles of palladous acetate and 10.7 millimoles of sodium nitrate in a 4-necked 100-cc flask equipped with a thermometer, a stirrer, a gas inlet and a reflux condenser, the contents were heated to 80° C. This was followed by blowing ethylene into the foregoing mixture for 20 minutes at the rate of 5 liters per hour, with stirring. After cooling the reaction mixture to room temperature, the product was analyzed by means of gas chromatography with the following results:

| | |
|---|---|
| acetaldehyde | 0.4 millimole |
| vinyl acetate | 1.0 millimole |
| ethylidene diacetate | 3.2 millimole |
| ethylene glycol diacetate | 1.8 millimole |
| ethylene glycol monoacetate | 8.0 millimole |

It can be seen from the foregoing results that the foregoing reaction proceeds catalytically by means of palladous acetate and that acetic acid esters of ethylene glycol can be obtained selectively.

On the other hand, when, by way of comparison, the reaction was carried out according to the procedure described in Example 1, using, instead of sodium nitrate, sodium acetate and sodium chloride in respectively equimolar quantity as the sodium nitrate, no formation at all of acetic acid esters of ethylene glycol was noted in either instance. Further, neither was there observed any formation of these esters in the case where the palladous chloride-sodium acetate catalyst system was used. In these comparative experiments, acetaldehyde, vinyl acetate and ethylidene acetate were formed in stoichiometrical quantities to the palladous acetate.

EXAMPLE 2

Except that 10.7 millimoles of sodium nitrate was used instead of sodium nitrate, the reaction was otherwise carried out as in Example 1. When the product was analyzed by means of gas chromatography, it was found that the following components were obtained.

| | |
|---|---|
| acetaldehyde | 0.3 millimole |
| vinyl acetate | 2.5 millimole |
| ethylidene acetate | 1.6 millimole |
| ethylene glycol diacetate | 1.5 millimole |
| ethylene glycol monoacetate | 2.0 millimole |

It therefore can be seen that the reaction in this case also proceeded catalytically.

EXAMPLE 3

The apparatus used in Example 1 was charged with 50 ml of glacial acetic acid, 4.3 millimoles of palladous nitrate, 35 millimoles of sodium nitrate and 25 millimoles of cupric acetate, following which the contents were heated to 100° C. The reaction was then carried out by blowing ethylene into the foregoing mixture for 2 hours at the rate of 10 liters per hour, with stirring. When the product was analyzed by means of gas chromatography after the reaction, it was found that the following compounds were obtained.

| | |
|---|---|
| acetaldehyde | 2.5 millimoles |
| vinyl acetate | 0.7 millimoles |
| ethylidene diacetate | 6.8 millimoles |
| ethylene glycol diacetate | 9.7 millimoles |
| ethylene glycol monoacetate | 6.0 millimoles |

EXAMPLE 4

The apparatus described in Example 1 was used, to which were charged 50 ml of acetic acid, 5.8 millimoles of palladous nitrate, 10.7 millimoles of lithium nitrate and 5.0 millimoles of nitric acid. The reaction was then carried out by blowing in ethylene for 20 minutes at 100° C.

As the product were obtained the following compounds:

| | |
|---|---|
| ethylene glycol diacetate | 7.9 millimoles |
| ethylene glycol monoacetate | 11.2 millimoles |
| ethylidene diacetate | 2.9 millimoles |
| vinyl acetate | 1.2 millimoles |
| acetaldehyde | 0.8 millimoles |

EXAMPLE 5

Fifty milliliters of propionic acid, 5 millimoles of palladous chloride and 15 millimoles of sodium nitrate were dissolved in the apparatus described in Example 1, following which ethylene was introduced thereinto for one hour at 100° C. Thus were obtained 5.4 millimoles of ethylene glycol dipropionate and 4 millimoles of ethylene glycol monopropionate.

EXAMPLE 6

Example 4 was repeated except that the reaction was carried out for 20 minutes at 100° C. after a further addition of 5 millimoles of barium acetate.

A product composed of the following components was obtained.

| | |
|---|---|
| ethylene glycol diacetate | 16.6 millimoles |
| ethylene glycol monoacetate | 19.1 millimoles |
| ethylidene diacetate | 3.0 millimoles |
| vinyl acetate | 1.3 millimoles |
| acetaldehyde | 0.9 millimoles |

EXAMPLE 7

When the reaction was carried out as in Example 1 except that a further addition of 5 millimoles of sodium acetate was made, the products obtained were as follows:

| | |
|---|---|
| ethylene glycol diacetate | 3.0 millimoles |
| ethylene glycol monoacetate | 13.3 millimoles |
| vinyl acetate | 1.1 millimoles |
| acetaldehyde | 0.6 millimoles |
| ethylidene diacetate | 2.5 millimoles |

EXAMPLE 8

When Example 1 was repeated except that 5.4 millimoles of cupric nitrate were used instead of sodium nitrate, the products obtained were as follows:

| | |
|---|---|
| ethylene glycol diacetate | 2.9 millimoles |
| ethylene glycol monoacetate | 4.5 millimoles |
| vinyl acetate | 0.8 millimoles |
| ethylidene diacetate | 0.9 millimoles |
| acetaldehyde | 0.5 millimoles |

EXAMPLE 9

An apparatus, as employed in Example 1, was charged with 50 cc of acetic acid (containing 5 mol % of water), one millimole of palladous chloride and 50 millimoles of lithium nitrate, following which the mixture was heated at 50° C. Ethylene was then blown into the foregoing reaction solution for 2 hours at the rate of 5 liters per hour, with stirring to accomplish the reaction.

When the resulting product was analyzed by means of gas chromatography, it was found to contain the following components:

| | |
|---|---|
| ethylene glycol monoacetate | 29.1 millimoles |
| acetaldehyde | 4.1 millimoles |
| ethylidene diacetate | 1.5 millimoles |
| ethylene glycol diacetate | 1.5 millimoles |

EXAMPLE 10

The apparatus of Example 1 was employed and by following the procedure described in Example 9 the reaction was carried out for 2 hours at 50° C. using one millimole of palladous acetate instead of palladous chloride, 50 millimoles of sodium nitrate and 20 millimoles of lithium acetate. When the product was similarly analyzed by means of gas chromatography, it was found to contain the following components:

| | |
|---|---|
| ethylene glycol monoacetate | 37.6 millimoles |
| ethylene glycol diacetate | 2.1 millimoles |
| acetaldehyde | 3.8 millimoles |
| ethylidene diacetate | 1.5 millimoles |

EXAMPLE 11

Except that a further addition of 10 millimoles of nitric acid was made to the reaction system of Example 9, the reaction was otherwise carried out at 2 hours at 50° C. as therein described. When the product was analyzed by means of gas chromatography after the reaction, it was found that it contained the following components:

| | |
|---|---|
| ethylene glycol monoacetate | 41.5 millimoles |
| acetaldehyde | 6.8 millimoles |
| ethylidene diacetate | 2.0 millimoles |
| ethylene glycol diacetate | 3.3 millimoles |

EXAMPLE 12

Fifty cc of acetic acid, one millimole of palladous nitrate, 50 millimoles of sodium nitrite, 20 millimoles of barium acetate and 20 millimoles of nitric acid were charged to an apparatus as employed in Example 1, after which the mixture was heated to 45° C. The reaction was then carried out for one hour while blowing in ethylene at the rate of 5 liters per hour. When the resulting product was similarly analyzed by means of gas chromatography after the reaction, the following products were obtained.

| | |
|---|---|
| ethylene glycol monoacetate | 32.0 millimoles |
| acetaldehyde | 5.7 millimoles |
| ethylidene diacetate | 6.5 millimoles |
| ethylene glycol diacetate | 1.9 millimoles |

EXAMPLE 13

Example 9 was repeated except that 50 cc of propionic acid were used instead of acetic acid. After a reaction of 2 hours, the resulting products were as follows:

| | |
|---|---|
| ethylene glycol monopropionate | 17.2 millimoles |
| acetaldehyde | 3.3 millimoles |
| ethylidene propionate | 0.8 millimoles |
| ethylene glycol dipropionate | 1.1 millimoles |

EXAMPLE 14

Example 9 was repeated excepting that the reaction was carried out for 2 hours at 95° C. instead of 50° C. When the resulting product was analyzed by means of gas chromatography, it was found to be composed of the following components:

| | |
|---|---|
| ethylene glycol deacetate | 13.6 millimoles |
| ethylene glycol monoacetate | 8.3 millimoles |
| acetaldehyde | 7.1 millimoles |
| ethylidene diacetate | 5.4 millimoles |
| vinyl acetate | 2.0 millimoles |

EXAMPLE 15

Employing an apparatus as described in Example 1, to which were added 50 cc of glacial acetic acid, 0.3 millimole of palladous chloride and 10 millimoles of lithium nitrate, the reaction was carried out for 6 hours at 45° C. while blowing into the mixture an ethyleneoxygen mixed gas (oxygen 30 mol %) at the rate of 3 liters per hour. When the product was analyzed by means of gas chromatography after the reaction, it was found to be composed of the following components:

| | |
|---|---|
| ethylene glycol monoacetate | 9.67 grams |
| acetaldehyde | 0.25 grams |
| ethylene glycol diacetate | 0.50 grams |
| ethylidene diacetate | 1.30 grams |
| vinyl acetate | 0.18 grams |

EXAMPLE 16

Except that 0.3 millimole of palladous acetate was used in instead of palladous chloride and 10 millimoles of sodium nitrite were used instead of lithium nitrate, the reaction was otherwise carried out for 5 hours using the apparatus and procedure described in Example 15, with the result that as reaction products the following compounds were obtained.

| | |
|---|---|
| ethylene glycol monoacetate | 5.4 grams |
| acetaldehyde | 0.05 grams |
| ethylidene diacetate | 0.40 grams |
| vinyl acetate | 0.11 grams |
| ethylene glycol diacetate | 0.3 grams |

EXAMPLE 17

A stainless steel shaking type 300-cc autoclave was charged with 100 cc of glacial acetic acid, 1.5 millimoles of palladous nitrate and 20 millimoles of lithium nitrate, after which the autoclave was heated until its internal temperature reached 40° C.

An ethylene-oxygen mixed gas (oxygen 17 mol %) was then introduced until a gauge pressure of 5 atm was built up, the reaction being carried out with shaking.

Since the pressure fell as the reaction produced, the pressure of 5 atm was maintained by successive introduction under pressure of a mixed gas of the aforesaid composition. The reaction was continued for one hour, whereby were obtained as products the following compounds:

| | |
|---|---|
| ethylene glycol monoacetate | 7.4 grams |
| acetaldehyde | 0.25 grams |
| vinyl acetate | 0.32 grams |
| ethylidene diacetate | 0.80 grams |
| ethylene glycol diacetate | 0.20 grams |

EXAMPLE 18

Except that propylene was used instead of ethylene, the reaction was otherwise carried out for 1 hour as in Example 15. Upon analysis of the product after the reaction, it was found that 2 grams of propylene glycol monoacetate, 0.1 gram of propylene glycol diacetate and 0.2 gram of acetone were formed.

EXAMPLE 19

The reaction was carried out for 5 hours in accordance with the procedure described in Example 15 except that 5 millimoles of calcium nitrate was added instead of lithium nitrate. 5.2 Grams of ethylene glycol monoacetate, 0.1 gram of ethylene glycol diacetate and 0.1 gram of acetaldehyde were detected from the reaction product.

EXAMPLE 20

The reaction was carried out for 5 hours as in Example 15 except that 5 millimoles of cupric nitrate were added instead of lithium nitrate. Four grams of ethylene glycol monoacetate and 0.1 gram of ethylene glycol diacetate were detected from the reaction product.

EXAMPLE 21

The reaction was carried out for 5 hours following the procedure described in Example 15, except that 5 millimoles of ferric nitrate were added instead of lithium nitrate, with the result that the reaction product yielded 3.8 grams of ethylene glycol monoacetate and 0.2 gram of ethylene glycol diacetate.

EXAMPLE 22

The reaction was carried out for 5 hours as in Example 15, except that 5 millimoles of nickel nitrate were added instead of lithium nitrate. 1.8 Grams of ethylene glycol monoacetate were obtained from the reaction product, while there was only a trace of ethylene glycol diacetate.

EXAMPLE 23

A 4-necked 200-cc flask equipped with a thermometer, a stirrer and a gas inlet was charged with 100 cc of glacial acetic acid, one millimole of palladous chloride and 5 millimoles of sodium nitrate, after which it was heated to 45° C. with stirring. The reaction was then carried out for 3 hours by blowing into the foregoing acetic acid mixture an ethylene-nitrogen dioxide mixed gas (mole ratio 8:2) at the rate of 10 liters per hour, with stirring. Since the internal temperature rose due to the heat of reaction, the flask was cooled with water and its temperature was maintained at 45° C. After the reaction, the product was analyzed by means of gas chromatography, and it was found that 9.1 grams of ethylene glycol monoacetate, 0.2 gram of ethylene glycol diacetate and 0.4 gram of acetaldehyde were formed.

EXAMPLE 24

The reaction was carried out for 7 hours following the procedure described in Example 23, excepting that an ethylene-oxygen-nitronic oxide mixed gas (mole ratio 3:1:1) was used instead of the ethylene-nitrogen dioxide mixed gas of Example 23, one millimole of palladous nitrate was used instead of palladous chloride and a further addition of 10 millimoles of lithium acetate was made. The reaction products obtained in this instance consisted of the following compounds:

| | |
|---|---|
| ethylene glycol monoacetate | 14.5 grams |
| ethylene glycol diacetate | 1.8 grams |
| acetaldehyde | 1.1 grams |
| ethylidene diacetate | 1.2 grams |

EXAMPLE 25

The apparatus described in Example 23 was employed, to which were charged 100 cc of acetic acid, one millimole of palladous acetate and 5 millimoles of lithium acetate. To this mixture were blow in at 45° C. an ethylene-oxygen mixed gas (mole ratio 2:1) at the rate of 5 liters per hour and separately nitronic oxide at the rate of 0.25 liter per hour. After a reaction of 3 hours, the products consisted of 12.7 grams of ethylene glycol monoacetate and 0.6 gram of acetaldehyde. The reaction was then continued for a further 3 hours in which the introduction of the nitronic oxide was stopped but the ethylene-oxygen mixed gas (mole ratio 2:1) was blown in at the rate of 5 liters per hour. The increase in the formation of ethylene glycol monoacetate after the completion of the additional 3 hours of the reaction was 9.9 grams while the increase of the acetaldehyde was 0.4 gram. In this case, hardly any formation of ethylene glycol diacetate was noted.

EXAMPLE 26

A 4-necked 2-liter flask equipped with a thermometer, a stirrer, a reflux condenser and a gas inlet was charged with 1.5 liters of glacial acetic acid, 3 grams of metallic palladium, 15 grams of lithium nitrate and 20 grams of lithium acetate, after which the mixture was heated to 60° C with stirring. The reaction was then carried out for 10 hours by continuously blowing into the mixture ethylene, oxygen and nitronic oxide separately at the rates of 20 leters, 10 liters and 0.3 liter per hour, respectively, with stirring. The so obtained reaction product consisted of the following compounds:

| | |
|---|---|
| ethylene glycol monoacetate | 530 grams |
| ethylene glycol diacetate | 40 grams |
| ethylidene diacetate | 60 grams |
| acetaldehyde | 16 grams |
| vinyl acetate | 1 grams |

EXAMPLE 27

In an apparatus as employed in Example 1 were dissolved 50 ml of glacial acetic acid, one millimole of palladous acetate and 50 millimoles of lithium nitrate, after which the contents were heated to 118° C. (boiling point of acetic acid). Ethylene was then blown into the foregoing mixture for 2 hours at the rate of 2 liters per hour with stirring. When, after cooling the reaction mixture to room temperature, it was analyzed by means of gas chromatography, it was found that 3.5 millimoles of acetaldehyde, 0.2 millimole of vinyl acetate, 4.6 millimoles of ethylidene diacetate, 30.7 millimoles of ethylene glycol diacetate and 7.1 millimoles of ethylene glycol monoacetate had been obtained.

What is claimed is:

1. A process for preparing glycol esters from a monoolefin selected from alpha-monoolefinic aliphatic hydrocarbons having up to 8 carbon atoms and styrene, which consists essentially of contacting said monoolefin with a solution of a palladous salt and at least one compound selected from alkali metal nitrates and nitrites in an organic acid selected from alkanoic acids having not more than 7 carbon atoms and benzoic acid at a temperature ranging from 20° to 150° C.

2. A process for selectively preparing glycol monoesters which consists essentially of contacting a monoolefin selected from alpha-monoolefinic aliphatic hydrocarbons having up to 8 carbon atoms and styrene with a solution of a palladous salt and at least one compound selected from alkali metal nitrates and nitrites in an organic acid selected from alkanoic acids having not more than 7 carbon atoms and benzoic acid at a temperature ranging from 20° to 80° C.

3. A process for selectively preparing glycol diesters which consists essentially of contacting a monoolefin selected from alpha-monoolefinic aliphatic hydrocarbons having up to 8 carbon atoms and styrene, with a solution of a palladous salt and at least one compound selected from alkali metal nitrates and nitrites in an organic acid selected from alkanoic acids having not more than 7 carbon atoms and benzoic acid at a temperature ranging from 80° to 150° C.

4. The process of claim 1 wherein said alpha-monoolefinic aliphatic hydrocarbons are selected from ethylene, propylene, and 1-butene and said alkanoic acids are selected from acetic acid, propionic acid, and butyric acid.

5. The process of claim 1 wherein said alkali metal nitrates and nitrites are selected from the lithium and sodium nitrates and nitrites.

6. The process of claim 1 wherein the reaction is effected in the presence of an organic monocarboxylic acid salt of a metal selected from the group consisting of the alkali and alkaline earth metals.

7. The process of claim 1 wherein the reaction is effected in the presence of oxygen.

8. The process of claim 1 wherein said palladous salt is a member selected from the group consisting of palladous chloride, palladous acetate and palladous nitrate.

9. The process of claim 1 wherein metallic palladium is added to the reaction system to form in situ said palladous salt.

10. The process of claim 1 wherein said alpha-monoolefinic hydrocarbon is ethylene.

11. The process of claim 1 wherein said organic acid is acetic acid.

12. The process of claim 1 wherein the concentration of said palladous salt in the reaction mixture of at least 0.001 percent by weight is used.

13. The process according to claim 1 wherein the concentration of said nitrates or nitrites in the reaction mixture of at least 0.001 mole per liter is used.

14. The process of claim 1 wherein the mole ratio of said nitrates or nitrites to said palladous salt in terms of $NO_3$ or $NO_2$:Pd of at least 1:1 is used.

15. The process of claim 14 wherein the mole ratio of said nitrates or nitrites to said palladous salt in terms of $NO_3$ or $NO_2$:Pd ranges between 5:1 and 100:1.

* * * * *